(12) United States Patent
de la Torre et al.

(10) Patent No.: US 6,840,951 B2
(45) Date of Patent: Jan. 11, 2005

(54) LAPAROSCOPIC ACCESS PORT FOR SURGICAL INSTRUMENTS OR THE HAND

(75) Inventors: Roger A. de la Torre, St. Louis, MO (US); James Stephen Scott, St. Charles, MO (US); George D. Hermann, Los Gatos, CA (US); Thomas A. Howell, Palo Alto, CA (US); James E. Jervis, Atherton, CA (US); Kenneth H. Mollenauer, Santa Clara, CA (US); Roderick A. Young, Palo Alto, CA (US)

(73) Assignee: Etheicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/004,468

(22) Filed: Oct. 23, 2001

(65) Prior Publication Data

US 2002/0038077 A1 Mar. 28, 2002

Related U.S. Application Data

(63) Continuation of application No. 09/451,570, filed on Nov. 30, 1999, now Pat. No. 6,319,246, which is a continuation of application No. 08/902,144, filed on Jul. 29, 1997, now Pat. No. 6,024,736, which is a continuation of application No. 08/319,986, filed on Oct. 7, 1994, now Pat. No. 5,653,705.

(51) Int. Cl.[7] .............................................. A61B 17/08
(52) U.S. Cl. ............................................ 606/213; 606/1
(58) Field of Search .......................... 606/1, 151, 185, 606/213, 167, 191–200; 604/513, 533, 539, 317, 332, 335, 337–344, 405, 264, 288.01–288.04; 600/201, 204, 207, 210

(56) References Cited

U.S. PATENT DOCUMENTS

| | | |
|---|---|---|
| 2,305,289 A | 12/1942 | Coburg |
| 3,244,169 A | 4/1966 | Baxter |
| 4,024,872 A | 5/1977 | Muldoon |
| 4,188,945 A | 2/1980 | Wenander |
| 4,308,864 A | 1/1982 | Small et al. |
| 4,991,593 A | 2/1991 | LeVahn |
| 4,998,538 A | 3/1991 | Charowsky et al. |
| 5,158,553 A | 10/1992 | Berry et al. |
| 5,196,003 A | 3/1993 | Bilweis |
| 5,211,370 A | 5/1993 | Powers |
| 5,213,114 A | 5/1993 | Bailey, Jr. |

(List continued on next page.)

FOREIGN PATENT DOCUMENTS

| | | |
|---|---|---|
| WO | WO 95/07056 | 3/1995 |
| WO | WO 95/22289 | 8/1995 |
| WO | WO 95/27445 | 10/1995 |
| WO | WO 95/27468 | 10/1995 |

OTHER PUBLICATIONS

Supplementary European Search Report, EP 96 93 3937, Oct. 2, 1998.

Inside Surgery, Medical Data International, vol. II, No. 1, pp. 117–120.

*Primary Examiner*—Glenn K. Dawson

(57) ABSTRACT

A flexible, fluid-tight envelope provides access for a hand and surgical instruments through a body tissue incision while maintaining insufflation pressure or a pneumoperitoneum within the body. The envelope is transparent and has an interior volume with opposite proximal and distal ends. A first opening in the envelope at the proximal end adjoins the incision in the body tissue and is secured and sealed to the body tissue. The second opening at the envelope distal end is provided with a closure member that seals closed the second opening on itself or around the forearm of a surgeon or a surgical instrument inserted into the interior volume of the envelope.

1 Claim, 7 Drawing Sheets

U.S. PATENT DOCUMENTS

| | | |
|---|---|---|
| 5,248,307 A | 9/1993 | Sokoloff |
| 5,257,973 A | 11/1993 | Villasuso |
| 5,299,582 A | 4/1994 | Potts |
| 5,316,541 A | 5/1994 | Fischer |
| 5,336,193 A | 8/1994 | Rom et al. |
| 5,366,478 A | 11/1994 | Brinkerhoff et al. |
| 5,368,545 A | 11/1994 | Schaller et al. |
| 5,385,560 A | 1/1995 | Wulf |
| 5,391,156 A | 2/1995 | Hildwein et al. |
| 5,407,427 A | 4/1995 | Zhu et al. |
| 5,423,848 A * | 6/1995 | Washizuka et al. ......... 606/185 |
| 5,437,683 A | 8/1995 | Neumann et al. |
| 5,480,410 A | 1/1996 | Cuschieri et al. |
| 5,514,133 A | 5/1996 | Golub et al. |
| 5,524,644 A | 6/1996 | Crook |
| 5,526,536 A | 6/1996 | Cartmill |
| 5,531,758 A | 7/1996 | Uschold et al. |
| 5,634,911 A | 6/1997 | Hermann et al. |
| 5,636,645 A | 6/1997 | Ou |
| 5,640,977 A * | 6/1997 | Leahy et al. ................ 128/897 |
| 5,653,705 A | 8/1997 | de la Torre et al. |
| 5,803,921 A | 9/1998 | Bonadio |
| 6,024,736 A * | 2/2000 | De La Torre et al. .......... 606/1 |
| 6,319,246 B1 * | 11/2001 | De La Torre et al. .......... 606/1 |

\* cited by examiner

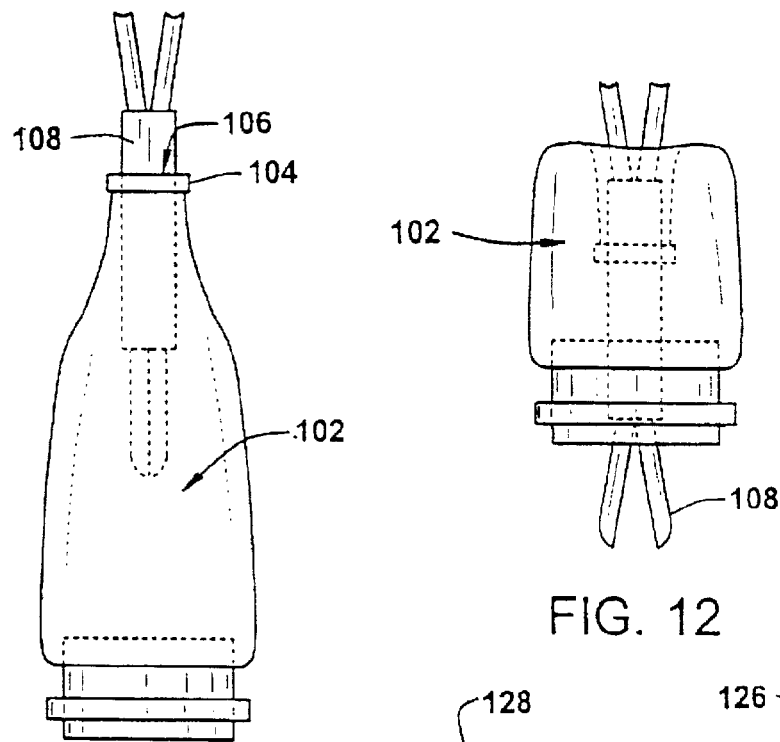
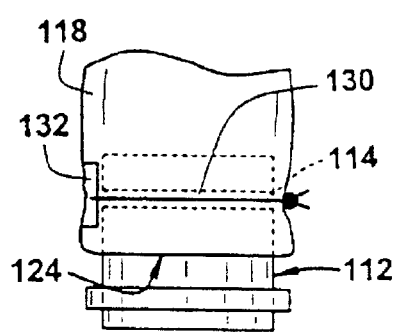
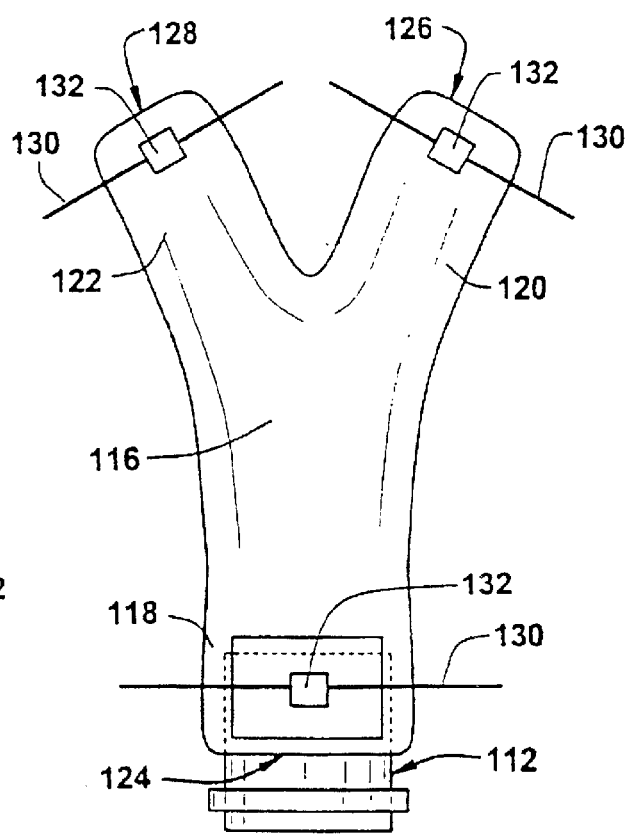
FIG. 11
FIG. 12
FIG. 13
FIG. 14

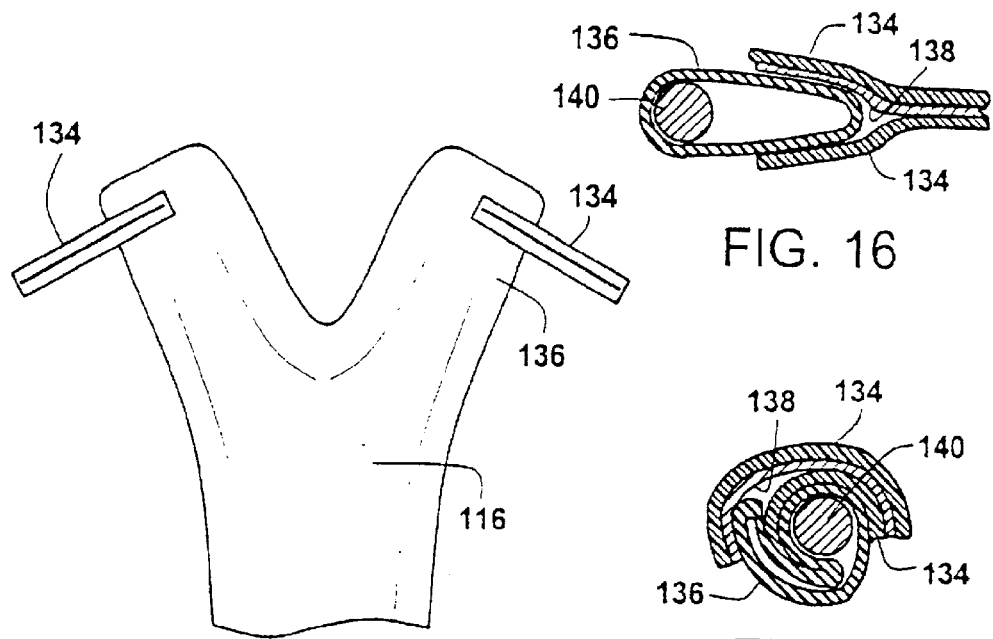
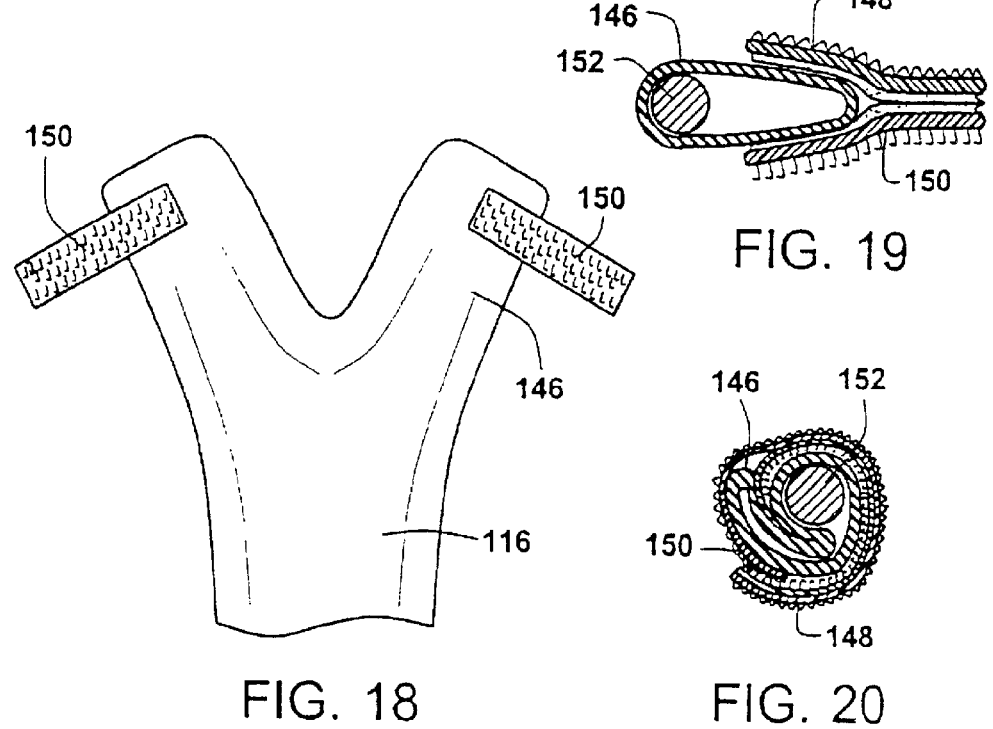

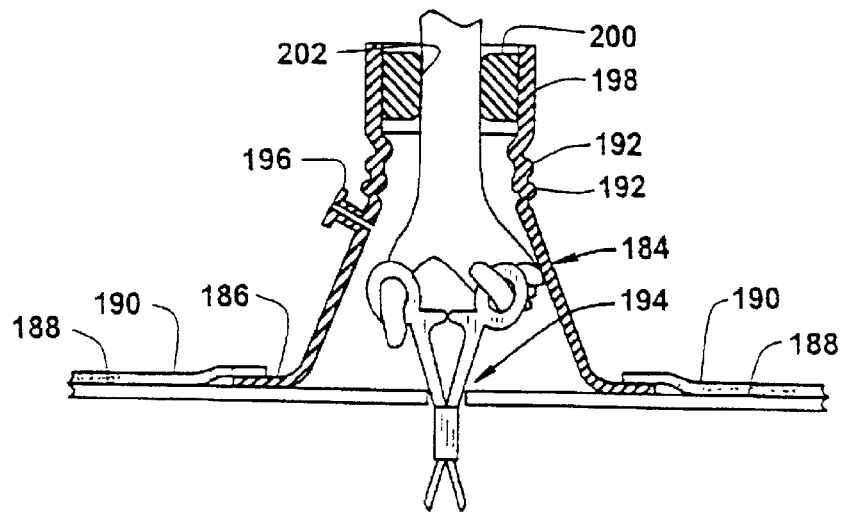
FIG. 24
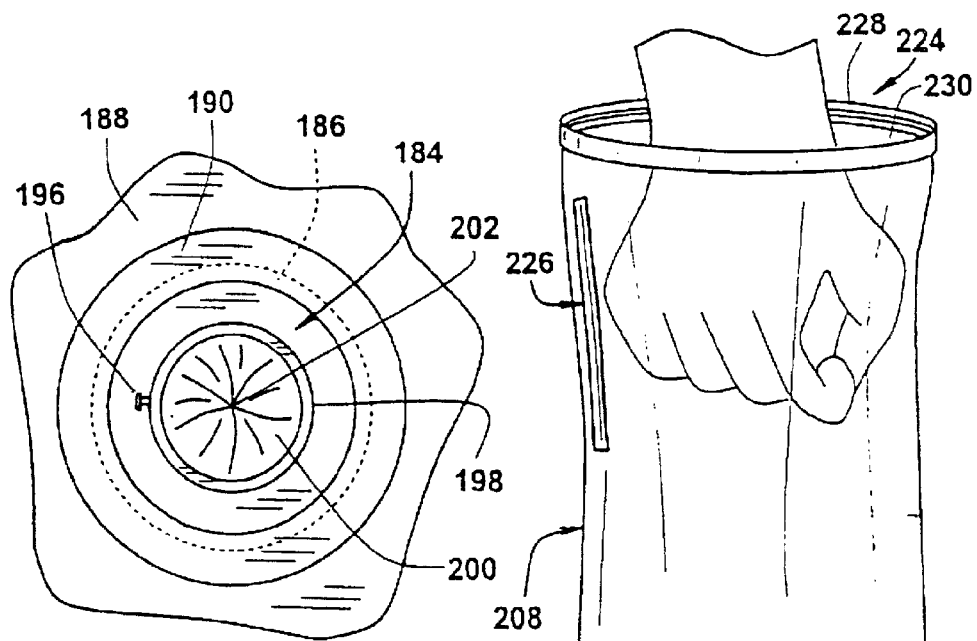
FIG. 25
FIG. 26

LAPAROSCOPIC ACCESS PORT FOR SURGICAL INSTRUMENTS OR THE HAND

This application claims priority from continuation application U.S. Ser. No. 09/451,570, which was filed on Nov. 30, 1999 and issued as U.S. Pat. No. 6,319,246 on Nov. 20, 2000, which is a continuation application U.S. Ser. No. 08/902,144, which was filed on Jul. 29, 1997 and issued as U.S. Pat. No. 6,024,736 on Feb. 15, 2000, which is a continuation application of U.S. Ser. No. 08/319,986, which was filed on Oct. 7, 1994 and issued as U.S. Pat. No. 5,653,705 on Aug. 5, 1997.

BACKGROUND OF THE INVENTION

(1) Field of the Invention

The present invention pertains to an apparatus employed as an access port in minimally invasive surgery that enables the insertion of instruments or the hand through a small incision in body tissue while maintaining the insufflation pressure within a body cavity.

(2) Description of the Related Art

Minimally, invasive surgery, such as laparoscopy, despite its beneficial aspects, has some disadvantages. Surgery of this type involving the use of surgical instruments manipulated through trocars or cannula inserted through body tissue to a surgery site within a body cavity requires a great deal of manual dexterity and hand-eye coordination of the surgeon. Many years of practice are required before the surgeon develops a comfortable level of agility in manipulating surgical instruments inserted through trocars to the surgical site while observing the movements of the instruments through a laparoscope. Until this level of familiarity with surgery techniques is developed by the surgeon, minimally invasive surgery requires significantly more of the surgeon's time than would the same operation being performed in an open incision of the body.

Additionally, the need to maintain a pneumoperitoneum or insufflation pressure within the body cavity at the surgery site while instruments are removed from and inserted through trocars during surgery increases the time required for performing an operation by minimally invasive surgery over that required for performing the same operation through an open incision in the body.

It is an object of the present invention to provide a surgical apparatus and its method of use that assist the surgeon in performing minimally invasive surgery by providing an access port through body tissue to a body cavity at the surgery site which enables insertion of surgical instruments or the surgeon's hand through the access port while maintaining the insufflation pressure or pneumoperitoneum within the body cavity.

SUMMARY OF THE INVENTION

The surgical apparatus of the present invention is basically comprised of a flexible, fluid-tight envelope having a hollow interior and first and second openings at opposite proximal and distal ends of the envelope. In the preferred embodiment, the envelope is transparent. A pair of tubular collars are secured to the opening at the proximal end of the envelope. The collars have coaxial interior bores and are connected to each other for relative rotation. The collars are provided with means for securing the collars to body tissue with the interior bores of the collars adjoining an incision through the tissue.

The distal end of the envelope is provided with means for selectively closing and sealing the second opening, or for opening the second opening to enable insertion of an instrument or the surgeon's hand into the envelope interior. With an instrument or the surgeon's hand inserted through the second opening, the means for sealing the opening is then secured around the envelope distal end and the instrument or hand to prevent the escape of insufflation pressure from the body cavity through the incision and the envelope. Several means of sealing closed the second opening of the envelope are provided including a slit second opening in the resilient material of the envelope that closes the opening in its at rest condition and is opened by stretching the material of the envelope. Various types of bands including elastic cords, strips containing malleable wire, and strips of hook and loop fastener material such as Velcro® are also secured around the distal end of the envelope to close and seal the envelope second opening.

Various embodiments of the concentric collars at the envelope proximal end are also employed in sealingly securing the envelope to the body tissue adjoining the tissue incision. These embodiments include a tapered portion of one of the collars which is wedged into the tissue incision to provide the sealed connection of the envelope to the tissue. A further embodiment employs an annular rim on one of the collars which is inserted through the incision to underlie the body tissue surrounding the incision. A panel having a circular center opening is then positioned over the collar and against the exterior of the body tissue to sandwich the tissue between the collar rim and the panel and thereby provide the sealed connection of the collars to the body tissue with the collars' interior bores adjoining the tissue incision. The embodiments of the collars are constructed of flexible plastic material that enables the collars to be clamped closed by a conventional grasper or forcep, thereby sealing closed the interior bores of the collars and enabling substitution of various embodiments of the envelope on the collars. A further embodiment of the collars is provided with a removable cap that closes over the collar interior bore sealing it closed.

One embodiment of the envelope has a general Y-shaped configuration with three projecting arms including one proximal arm and two distal arms. The proximal arm is provided with the first opening secured to the pair of collars and the two distal arms are provided with second and third openings and means on the distal arms for closing their openings as in the previously described embodiment of the envelope.

In use of each of the embodiments of the invention, an incision is made in the body tissue and the pair of collars are secured to the body tissue with the center bores of the collars adjoining the tissue incision. The second opening of the envelope is sealed closed. The body cavity at the site of the surgery to be performed is then insufflated. The sealed connection of the collars to the body adjoining the incision and the sealed closure of the envelope second opening maintains the insufflation pressure within the body cavity while providing an access port for insertion of instruments or the surgeon's hand into the body cavity.

Insertion of an instrument or the surgeon's hand into the body cavity is accomplished by releasing the sealed closure of the envelope second opening and inserting the instrument or hand into the envelope interior through the second opening. The second opening is then again sealed closed around the instrument or forearm of the hand inserted into the envelope. The instrument or hand may then be inserted through the interior bores of the collars secured to the body with the sealed closure of the second opening around the instrument or hand maintaining the insufflation pressure within the body cavity.

BRIEF DESCRIPTION OF THE DRAWINGS

Further objects and features of the present invention are revealed in the following detailed description of the preferred embodiment of the invention and in the drawing figures wherein:

FIGS. 11 and 12 show a further embodiment of the envelope of the invention;

FIGS. 13 and 14 show a further embodiment of the envelope of the invention;

FIGS. 15–17 show a further embodiment of the envelope of the invention;

FIGS. 18–20 show a further embodiment of the envelope of the invention;

FIGS. 24 and 25 show a further embodiment of the invention, and

FIG. 26 shows a further embodiment of the invention.

DESCRIPTION OF THE PREFERRED EMBODIMENTS

Figure 1:
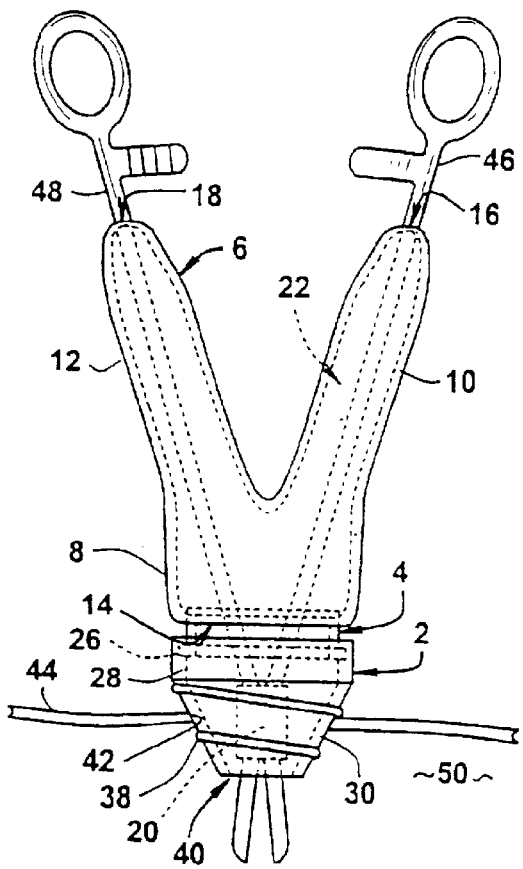
FIG. 1 shows a first embodiment of the invention in its operative position sealed to an incision made in body tissue and projecting into a body cavity.

A first embodiment of the apparatus of the invention is shown in FIG. 1 of the drawing figures. This embodiment is generally comprised of a first collar 2, a second collar 4, and a flexible, fluid-tight envelope 6. In the preferred embodiment of the invention, the three primary component parts set forth above are all constructed of flexible, resilient plastic materials. However, it should be understood that the apparatus of the invention may be constructed of various different types of materials acceptable for use in surgical instruments. Furthermore, the relative dimensions of the component parts of the invention shown in the drawing figures are illustrative only and should not be interpreted as limiting. The apparatus of the invention can be constructed in various different sizes without departing from the intended scope of the invention.

Preferably, the material of the envelope 6 is also transparent to enable the surgeon to observe the manipulation of an instrument or the surgeon's hand in the envelope. For example, the envelope could be formed from two overlapping layers of urethane film that are heat sealed together at their edges. Other equivalent materials and methods of construction may be employed. The envelope 6 has a general Y-shaped configuration with a first arm 8 at a proximal end of the envelope and second 10 and third 12 arms at the opposite distal end of the envelope. A first opening 14 is provided at the end of the envelope first arm 8 and the second collar 4 is received in the first opening. The second collar 4 and the envelope first arm are permanently secured together providing a sealed connection between the collar and envelope. Alternatively, the envelope first arm could overlap the top of the collar and be secured thereto by an elastic band or a length of suture tied around the arm and collar. The ends of the second and third arms 10, 12 are also provided with respective second 16 and third 18 openings therethrough. Means are provided at the ends of the second and third arms 10, 12 for selectively closing and sealing the respective second and third openings 16, 18. The manner of closing the second and third openings will be described in more detail with reference to later embodiments. The closures at the second and third openings 16, 18 enable these openings to be closed and sealed around surgical instruments such as the forceps 20 shown in FIG. 1. Alternatively, in a larger version of the apparatus shown in FIG. 1, the surgeon's hand and forearm can be inserted through the second opening 16 and the surgical instrument inserted into the envelope interior 22 through the third opening 18 to be grasped by the surgeon within the envelope. The second opening 16 may then be secured around the forearm of the surgeon and the third opening 18 closed and sealed to prevent the escape of insufflation pressure through the second and third openings in use of the apparatus.

The second collar 4 has a cylindrical configuration with a hollow, cylindrical interior bore extending therethrough. The interior bore 24 of the collar communicates with the interior volume 22 of the envelope. Opposite its connection to the envelope 6, the second collar has an annular flange 26 that extends around its exterior surface.

The first collar 2 is formed of two sections, a first section 28 having a cylindrical configuration and a second section 30 having a tapering configuration. The first section 28 has a cylindrical interior bore 32 with an annular groove 34 formed therein. The annular groove 34 is dimensioned to receive the annular flange 26 of the second collar, thereby providing a sealed rotatable connection between the first and second collars. As seen in FIG. 1, the second section 30 has a tapering interior bore 36 and a tapering exterior surface over which extends a helical thread 38. The first collar second section 30 tapers to an access opening 40 that provides access to the envelope interior volume 22 through the interior bores of the first and second collars 2, 4.

Referring to FIG. 1, in use of this first embodiment of the apparatus of the invention, an incision 42 is first made through body tissue 44. The first collar 2 is then secured in the incision by first inserting the tapered section 30 of the collar into the incision 42 and rotating the collar, causing the helical thread 38 to pull the collar 2 further into the incision. The incision 42 in the body tissue 44 is stretched around the exterior of the first collar 2 as the collar is turned and effectively screwed into the incision. The snug fit of the first collar tapered section 30 in the incision 42 secures the apparatus to the body tissue and seals the connection of the apparatus to the tissue. Alternatively, the first collar may be secured to the body tissue by adhesive tape, or may be sutured to the tissue. The first collar 2 may be provided with a cannula extension (not shown) from its access opening 40 to reach through all skin layers. The first collar 2 may be secured to the tissue 44 by its being wedged in the incision 42 with the second collar 4 and envelope 6 attached, or with the second collar and envelope removed. In the later case, the flexibility and resiliency of the first and second collars enables the second collar 4 to be later attached to the first collar 2 inserting the annular flange 26 of the second collar into the annular groove 34 of the first collar. The second and third openings 16, 18 of the envelope 6 are closed to seal the envelope interior volume 22. If so desired, an instrument such as the forcep 20 may first be inserted into the envelope interior through one of the first or second openings 16, 18 and then positioned in the envelope with each of its handles 46, 48 projecting through the first and second openings. The first and second openings are then sealed closed around the handles of the forcep.

Figure 3:
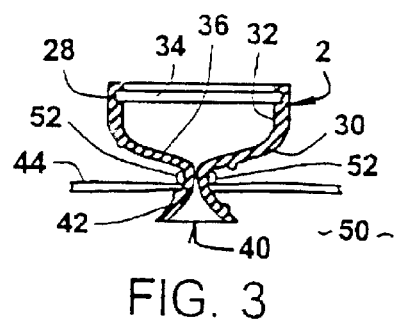
FIG. 3 is an in-section view of a collar of the FIG. 1 embodiment clamped closed.

Following the setup of the apparatus of the invention described above, insufflation pressure is then supplied to the body cavity 50. The insufflation pressure passes through the incision and also inflates the envelope. If it is later necessary to remove the forceps 20 or the envelope 6 for its replacement with another embodiment of envelope to be described later, the resilient material of the first and second collars 2, 4 enable the collars to be clamped closed with the jaws 52 of a surgical clamp as illustrated in FIG. 3. This seals closed the access port provided by the apparatus of the invention maintaining the insufflation pressure while the envelope is replaced on the first collar 2. Alternatively, the first collar could be provided with a valve assembly.

Because insufflation pressure is low, typically 10 mm of mercury (Hg), various different types of valve assemblies may be employed in the first collar bore to maintain insufflation pressure in the body cavity. For example, an inflatable toroid-shaped balloon which closes at its inside diameter when inflated may be employed as the valve. Also, a foam disk having a center aperture which closes due to the resiliency of the foam may also be employed as the valve. In both examples, the flexibility of the balloon or foam allow insertion of the hand and/or instruments through the center opening. The resiliency of the balloon or foam causes the center opening to seal around the hand or instrument inserted through the opening, and causes the opening to seal closed once the hand or instrument is removed. Various other types of value structures may also be employed.

Figure 2:
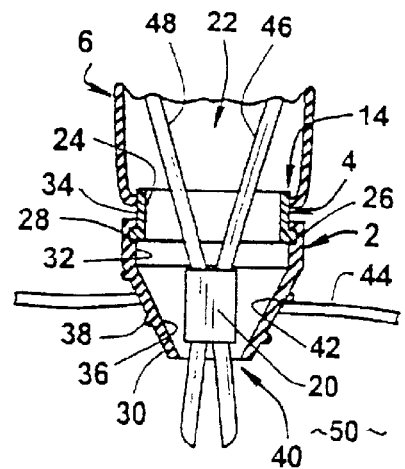
FIG. 2 is a partial, in-section view of the embodiment of FIG. 1.
Figure 4:
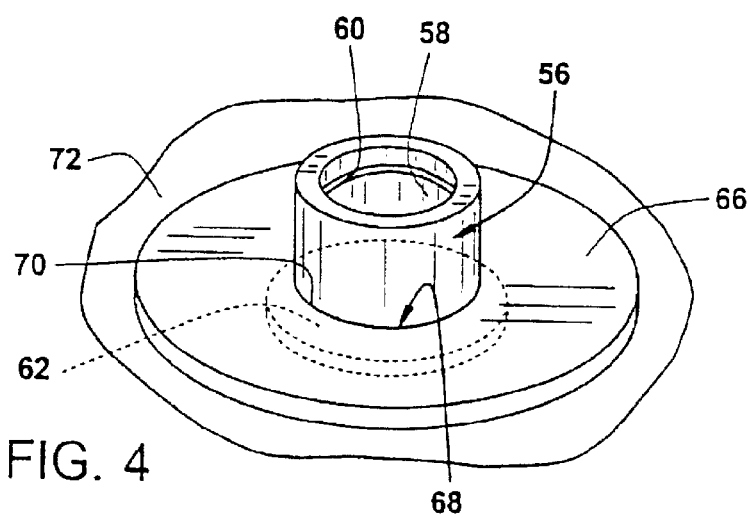
FIG. 4 is a perspective view of a second embodiment of one of the collars of the invention.

FIG. 4 shows an alternative to the first collar 2 of the apparatus of FIGS. 1–3. In FIG. 4, the first collar 56 again has a cylindrical configuration with a cylindrical interior bore 58 having an annular groove 60 dimensioned to receive the annular flange 26 of the second collar 4 of the apparatus of FIGS. 1–3. However, instead of a tapered section of a collar, this embodiment of the first collar has an annular rim 62 adjacent its access opening 64. A circular panel 66 having a circular center opening 68 is positioned over the collar 56 with the collar extending in a tight, friction fit through the panel opening 68. Together, the annular rim 62 and panel 66 secure this embodiment of the first collar 56 to the body tissue with the collar extending through the incision in the tissue.

Figure 5:
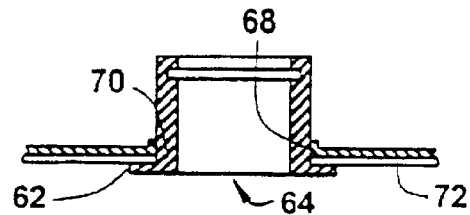
FIG. 5 is a cross section of the collar of FIG. 4.
Figure 6:
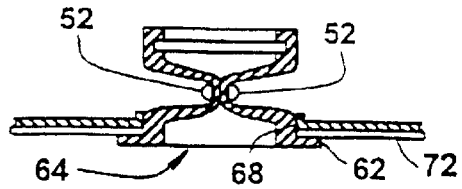
FIG. 6 is a cross section of the collar of FIG. 4 showing the collar clamped closed.

In use of the embodiment of FIGS. 4–6, the flexible resiliency of the material of a collar enables the collar rim 62 to be deformed and inserted through a small incision 70 made in the body tissue 72. The resiliency of the collar enables it to expand once inserted through the incision 70 so that the incision is stretched around the periphery of the collar 56 and the annular rim 62 extends beneath the body tissue surrounding the incision. The panel 66 is then positioned over the collar 56 with the collar inserted through the panel opening 68. With the panel pushed down over the collar, the tight-friction fit of the panel 66 around the collar secures the collar to the body tissue 72 and seals the incision between the collar rim 62 and the panel 66. With the collar in place, the second collar 4 and envelope 6 may then be attached to the first collar in preparation for use as described earlier with reference to the first embodiment.

Like the first collar of the first embodiment, the first collar embodiment of FIGS. 4–6 may also be sealed closed by crimping the collar between the jaws 52 of a surgical grasper as illustrated in FIG. 6, thereby sealing closed the collar interior bore 58 and maintaining the insufflation pressure in the body cavity when the envelope is removed from the collar.

Figure 7:
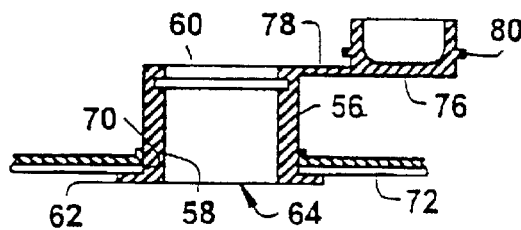
FIGS. 7 and 8 show a variant embodiment of the collar of FIG. 4.
Figure 8:
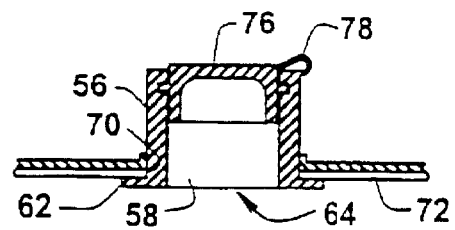

Alternatively, the first collar may be provided with a sealing cap 76 as shown in FIGS. 7 and 8. The cap 76 is connected by a flexible tether 78 to the collar 56. The cap 76 has an annular flange 80 around its periphery that is dimensioned to fit the annular groove 60 of the first collar with the cap inserted into the collar interior bore, thereby sealing closed the interior bore of the collar.

FIGS. 9–23 show various embodiments of the envelope, all of which may be employed with the first described embodiment of the first collar 2 shown in FIGS. 1–3 or the second described embodiment of the first collar 56 shown in FIGS. 4–8.

Figure 9:
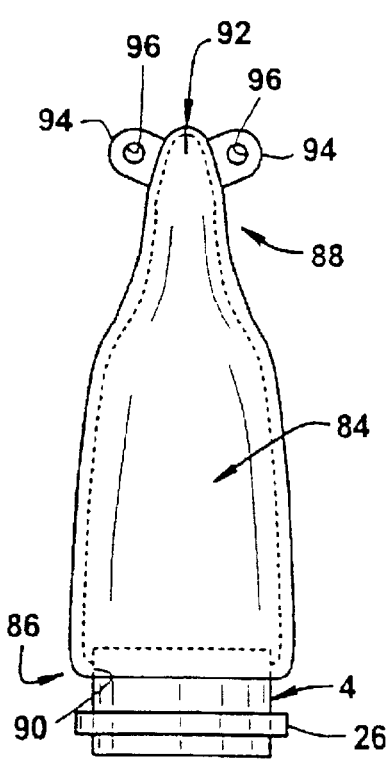
FIGS. 9 and 10 show a further embodiment of the envelope of the invention.
Figure 10:
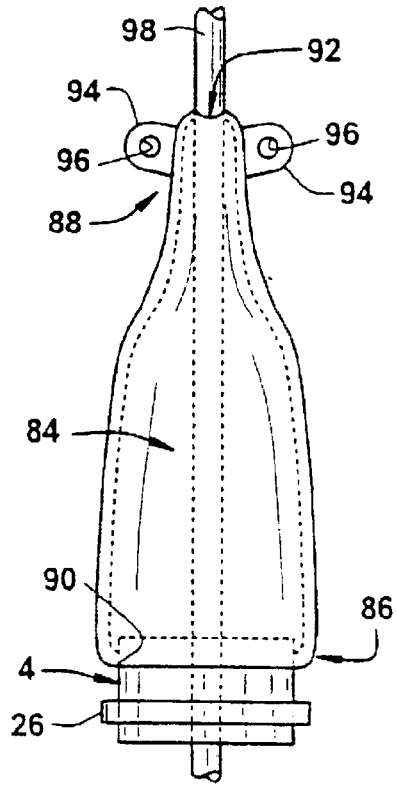

The embodiment of the envelope 84 shown in FIGS. 9 and 10 does not have the Y-shaped configuration of the first described embodiment of the envelope. The envelope 84 has opposite proximal 86 and distal 88 ends. The envelope proximal end 86 has a first opening 90 that is secured to a second collar 4 identical to the second collar of the first described embodiment. The connection between the envelope 84 and the second collar 4 is also identical to that of the first described embodiment. The material of the envelope 84 is transparent, flexible and fluid-tight as the first described envelope. However, this embodiment of the envelope employs a material that has resiliency enabling the material to be stretched from its at-rest configuration shown in FIG. 9.

The second opening 92 at the envelope distal end 88 is formed as a slit opening. In the at-rest condition of the envelope, the second opening 92 is closed. The resiliency of the envelope material is sufficient to maintain the second opening closed in its at-rest condition and prevent leakage of insufflation pressure, typically 10 mm of mercury (Hg), through the slit opening. A pair of ears 94 project from the envelope on opposite sides of the second opening 92. Each of the ears 94 has a hole 96 therethrough that can be engaged by a spreading tool to move the ears away from each other. Movement of the ears 94 away from each other stretches the slit opening 92 of the envelope open, enabling the insertion of instruments, such as the intermediate length of the surgical grasper 98 shown in FIG. 10, through the opening. The resiliency of the envelope material causes the slit opening 92 to close and seal around the grasper 98 when the ears 94 are released, thereby maintaining the insufflation pressure.

As in the first embodiment of the invention, the second collar 4 at the proximal end of the envelope 84 is provided with an annular flange 26 that engages in the annular groove of the first collar forming the sealed, rotating connection between the first collar and the envelope 84.

FIGS. 11 and 12 show an embodiment of the envelope 102 similar to the previously described embodiment of the envelope 84 of FIGS. 9 and 10. The difference between the embodiment of FIGS. 9 and 10 and that of FIGS. 11 and 12 is that the slit opening and ears of the previous embodiment are replaced by an elastic band 104 that surrounds the second opening 106 at the distal end of the FIGS. 11 and 12 envelope embodiment. The remaining construction of the envelope 102 and second collar 4 remains the same as previously described embodiments. In the embodiment of FIGS. 11 and 12, the elastic band 104 is stretched open to enable insertion of an instrument, such as the forceps 108, into the envelope second opening 102. The band 104 is then allowed to contract around the forceps 108 near the hinge point or box lock to essentially seal the second opening 106 around the forceps and maintain insufflation pressure. As shown in FIG. 12, the flexibility of the envelope material enables the envelope to be folded back in through its interior when reaching into the incision with the forceps.

In the embodiment of the envelope shown in FIGS. 13 and 14, the second collar 112 varies only slightly from the second collar of the previously described embodiments in that it has an annular groove 114 formed around its exterior surface. The remaining construction of the second collar and the manner in which it connects to the first collar for relative rotation therewith remains the same.

Various embodiments of the envelope may be removably attached to the embodiment of the second collar 112 shown in FIG. 13. The envelope 116 shown in FIGS. 13 and 14 again has the general Y-shaped configuration of the first described embodiment including the proximal arm 18 and two distal arms 120, 122. The proximal arm 118 has a first opening 124 to the interior volume of the envelope and the distal arms 120, 122 have second and third openings 126, 128 to the envelope interior. Connected to the proximal and distal arms adjacent their openings are flexible bands, in this embodiment lengths of elastic cord 130 secured adjacent the openings by sections of adhesive tape 132.

In securing the proximal arm 118 to the second collar 112, the collar is inserted through the first opening 124 of the arm and the length of cord 130 is positioned adjacent the collar external groove 114. The length of cord is then tightly bound around the envelope proximal arm 118 overlying the collar exterior groove 114 securely connecting the proximal arm of the envelope to the collar. The connection of the envelope arm to the collar in this manner provides a sufficient seal between the arm and collar to maintain insufflation pressure. The second and third openings 126, 128 of the distal arms 120, 122 are sealed closed in the same manner. The second and third openings may be sealed closed upon themselves, or may be sealed closed around the forearm of the surgeon or around a surgical instrument by binding the cords 130 around the distal arms in the same manner as described with reference to the proximal arm of the envelope 116.

The embodiments of the envelope shown in FIGS. 15–20 are substantially identical to that shown in FIGS. 13 and 14 except that other closure means are employed in lieu of the cord 130 employed in the FIGS. 13 and 14 embodiment.

In FIG. 15, two strips of adhesive tape 134 are secured to each of the envelope arms 136. A length of malleably metal 138, for example a length of wire, is sandwiched between the two pieces of tape. To close the openings at the ends of the two envelope distal arms 136, the tape containing the wire is wrapped around the arm and the instrument 140 inserted through the arm openings to securely seal the openings around the instrument as shown in FIG. 17. If an instrument is not inserted through the arm opening, the tape containing the wire is merely wrapped around the arm to seal closed the opening. The wire within the tape maintains the tape in its wrapped configuration around the envelope arm.

FIGS. 18–20 show a further embodiment in which the cords and tape of the previously described embodiments are replaced by hook and loop fasteners, for example Velcro® type fasteners. As shown in the drawing figures, each of the envelope distal arms 146 has the backside of a hook fastener strip 148 and a loop fastener strip 150 secured thereto. Portions of the backsides of the hook and loop fastener strips are also secured together. To seal closed the arm opening around an instrument 152 inserted through the opening, the hook and loop fasteners are wrapped around the envelope distal arm and the instrument inserted through the opening of the arm. This causes the hook strip 148 to overlap the loop strip 150 and thereby seal closed the arm opening around the instrument 152.

Although only the envelope distal arms are shown in FIGS. 15–20, it should be understood that the tape and wire closure shown in FIGS. 15–17 and the hook and loop closure shown in FIGS. 18–20 may be employed to removably secure the proximal arm to the second collar in lieu of the elastic cord 130 disclosed in the embodiment of FIGS. 13–14. Still further, the envelope openings at the proximal and distal ends of the envelope may be sealed closed in other equivalent manners than those disclosed above.

Figures 21, 22:
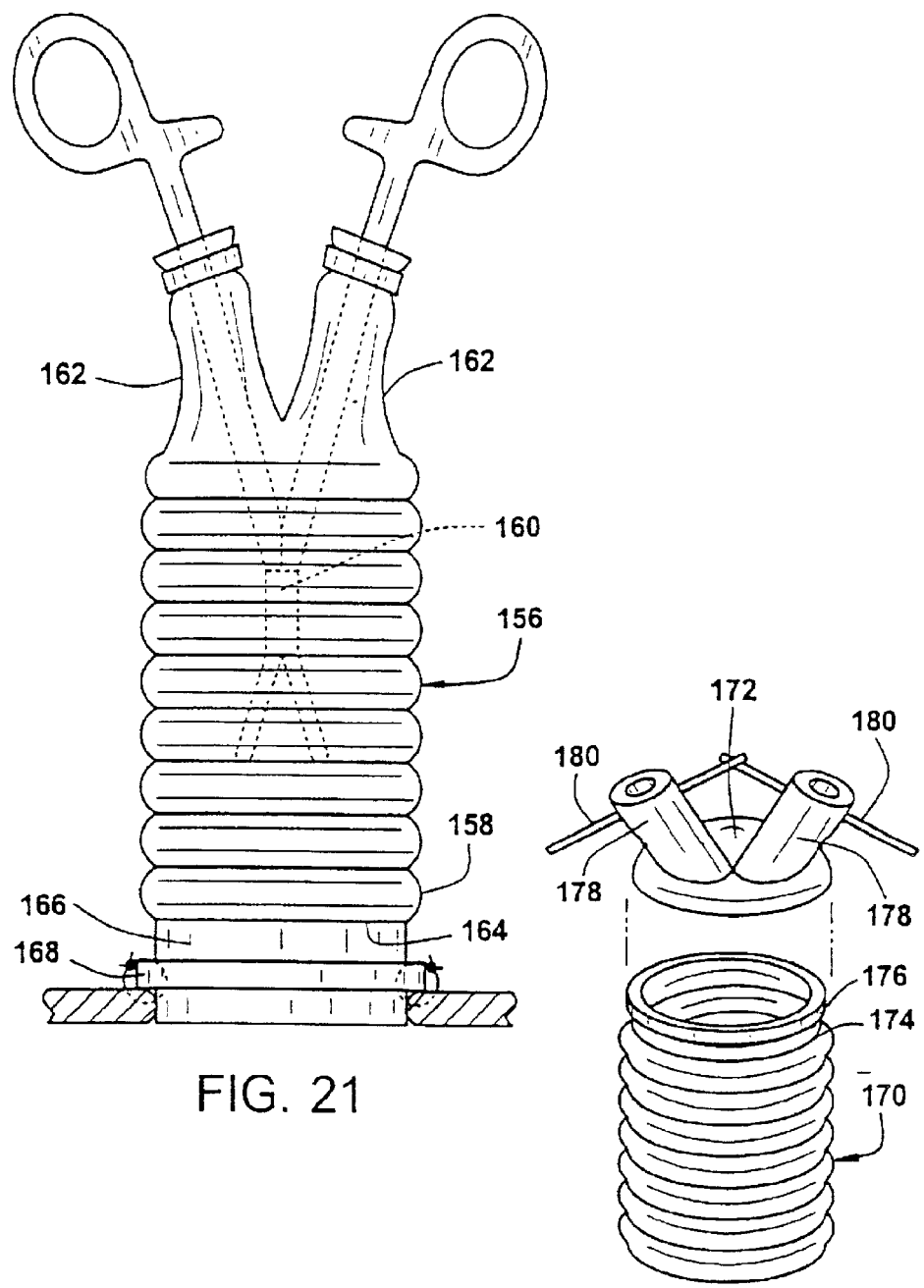
FIGS. 21–23 show a further embodiment of the envelope of the invention.

The envelope 156 of the FIG. 21 embodiment is similar to the previously described Y-shaped embodiments except that its first arm 158 is formed as a bellows with a plurality of pleats. The pleats formed in the first envelope arm 158 give it even more flexibility than the previously described embodiments and enable reaching deep into an incision with an instrument 160 by compressing the pleats of the bellows. Expanding the pleats of the bellows enables the instrument 160 to be withdrawn and spaced far from the incision with the expanding bellows pleats significantly increasing the interior volume of the envelope 156. The distal arms 162 of the envelope are secured and sealed to the handles of the instrument 160 in the same manner as any of the previously described embodiments. The proximal end of the envelope 164 is secured to a collar 166 that can be releasably attached to any of the previously described embodiments of the first collar. Additionally, the collar 166 can be secured directly to the body tissue surrounding the incision as shown in FIG. 21. The lower end of the collar is first inserted through the incision until the annular flange 168 of the collar abuts against the exterior surface of the tissue surrounding the incision. The collar may then be secured in place to the tissue incision by passing suture through the collar and the tissue surrounding the incision. Alternatively, the collar could be secured in place through the use of adhesive tape. In use of the collar in this manner, the lower end of the collar is extended to ensure that it reaches completely through the layer of skin tissue.

FIGS. 22 and 23 show a variation of the envelope of FIG. 21. In this embodiment, the envelope distal end has a circular cap 172 removable secured thereto. The cap is preferably constructed of a flexible plastic material and is provided with an interior annular groove (shown in dashed lines in FIG. 22) much the same as the annular groove provided in the first and second embodiments of the first collar 2, 56 described earlier. The distal end 174 of the envelope 170 has an annular flange 176 formed thereon dimensioned to mate in the annular groove on the interior of the cap 172. The insertion of the annular flange 176 into the cap annular groove provides a releasable, sealed connection between the envelope proximal end 174 and the cap 172.

Figure 23A:
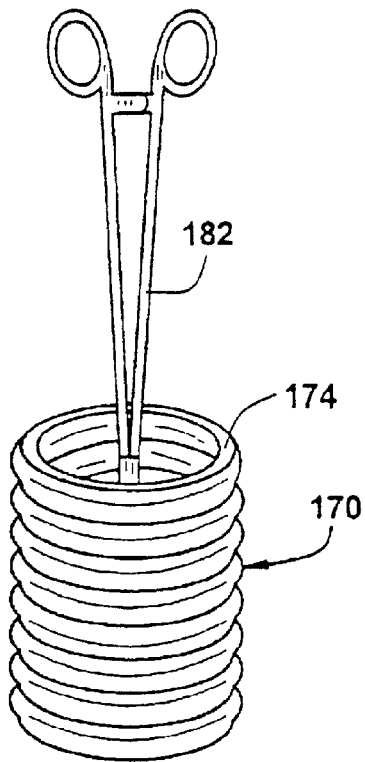
Figure 23B:
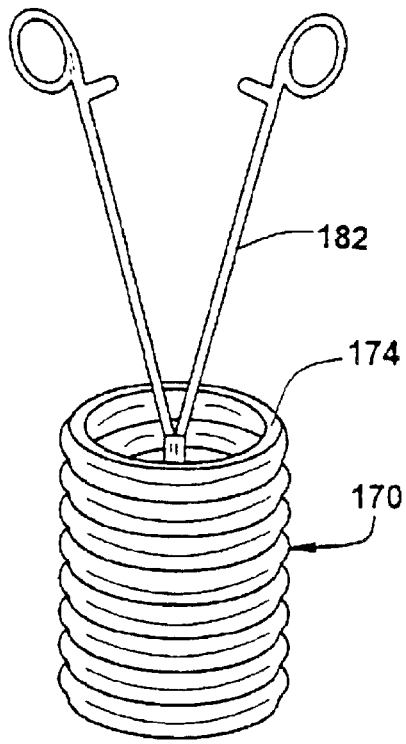
Figure 23C:
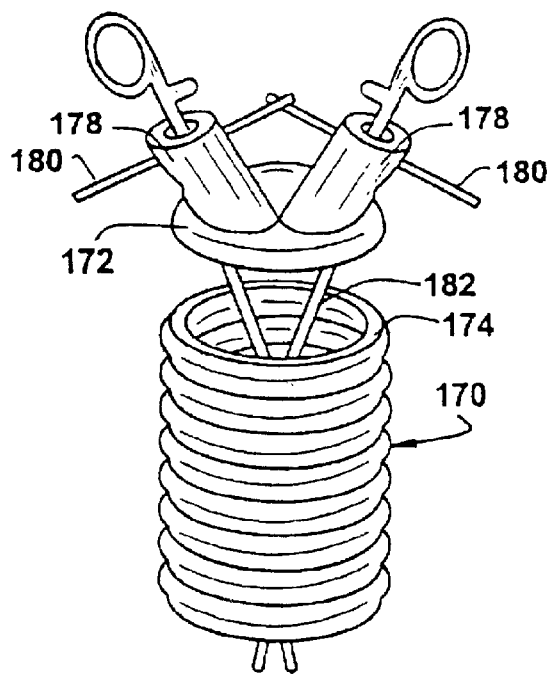
Figure 23D:
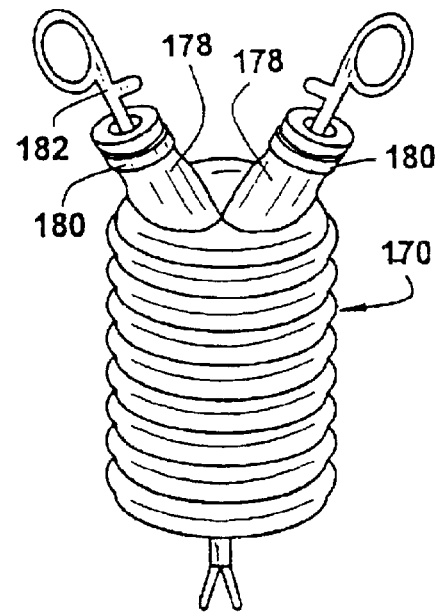

The cap 172 is also provided with a pair of distal arms 178. The arms 178 are also constructed of the flexible, resilient plastic material enabling the handles of an instrument to be inserted through the interiors of the arms as illustrated in FIG. 23C. Elastic cords 180 are secured to each of the arms 178 for securing the arms closed around the instrument handles as in the previous embodiments. Other equivalents of the cords 180 may also be employed in closing the arms 178 around the instrument handles.

By providing a detachable cap on the envelope, the pleated section of the envelope does not need to be very wide. The envelope can be much narrower if the instrument can be loaded into the envelope from the top. In this way, the handle rings of the instrument do not have to fit through the envelope. (See FIG. 23). Use of this embodiment of the invention is illustrated in FIGS. 23A–23D. The removable cap 172 is first removed from the proximal end of the envelope 170 exposing the envelope interior volume. The instrument 182 may then be inserted into the envelope. As shown in FIG. 23B, the interior volume of the envelope provides ample room for manipulation of the instrument. The cap 172 is then positioned over the instrument's handles inserting each of the handles through the arms 178 of the cap so that they project from the arms as illustrated in FIG. 23C. The cap 172 is then secured to the envelope distal end 174 by inserting the annular flange 176 into the interior annular groove of the cap as explained earlier. The cords 180 are next secured tight (e.g. by a simple half-hitch) around the arms 178 sealing the arms to the instrument handles. This embodiment of the invention is now ready for use in the same manner as the previously described embodiments.

FIGS. 24 and 25 show a further embodiment of the apparatus where the envelope of the apparatus is secured to the body tissue on the exterior surface of the tissue surrounding the incision. Referring to FIG. 24, this embodiment is comprised of an envelope 184 having a wide circular base with a projecting annular rim 186. The rim 186 is secured to the exterior surface of the body tissue 188 by adhesive strips 190. Alternatively, the rim 186 may be secured to the tissue 188 by suturing or other equivalent means. The envelope 184 extends upwardly from its base and tapers toward a bellows section having a plurality of circular pleats 192. The tapering of the envelope gives it a general conical configuration with a larger interior volume of the envelope positioned adjacent its annular rim 186 than the volume of the envelope adjacent the pleats 192. The pleats 192 enhance the flexibility of the envelope allowing it to expand away from the tissue incision 194 and compress toward the incision.

A port opening 196 passes through the side of the envelope just below the pleats 192. The port 196 is provided for gas insufflation of the body cavity accessible through the incision 194 and the interior volume of the envelope. A similar port may be provided on the envelopes of the previously described embodiments.

Just above the plurality of circular pleats 192 the distal end of the envelope is formed as a cylindrical sleeve 198. Positioned against the interior surface of the sleeve 198, is a valve 200 that seals closed around an instrument or a surgeon's hand inserted through the valve, or closes the center opening 202 of the valve when the instrument or hand is removed. The valve 200 may be a toroid of foam secured to the interior surface of the sleeve 198. The resilience of the foam enables its center opening 202 to expand when an instrument or the surgeon's hand is inserted through the opening, maintaining a sealed closure around the instrument or hand sufficient to maintain insufflation pressure in the body cavity and the envelope interior. The seal 200 may also be an inflatable bladder having a toroid shape which functions in the same manner as the foam toroid seal. Additionally, the toroid foam valve and the inflatable bladder toroid valve may be friction fit in and removable from the interior of the envelope sleeve 198. In this variation of the valve, it remains sealed around the hinge box of the surgical instrument or the surgeon's wrist as the instrument or wrist are removed from the interior of the envelope sleeve 198. In use of a valve of this type, the resilient material of the envelope 184 must be clamped closed by a surgical clamp as in previously described embodiments in order to maintain insufflation pressure in the body cavity as the instrument or wrist with attached seal are removed from the interior of the instrument sleeve 198. On reinsertion of the instrument or wrist with the attached seal back into the envelope interior with the toroid seal positioned in the envelope sleeve 198 interior, the clamp sealing closed the envelope may then be removed to permit access for the instrument through the tissue incision 194. The repositioned seal in the envelope sleeve 198 maintains insufflation pressure in the body cavity and the envelope interior.

FIG. 26 shows a still further embodiment of the apparatus of the invention. The embodiment of FIG. 26 is basically comprised of the flexible envelope 208 similar to previously described embodiments of the envelope, secured to a collar 210 which is also similar to previously described embodiments of the collar in FIGS. 1–23. The envelope 208 is shown permanently secured to the collar 210. However, the proximal end of the envelope 212 may be secured to the collar 210 in a variety of different manners such as the previously described embodiments. The upper end of the collar 210 may be inserted into the opening at the envelope proximal end 212 and the envelope secured around the collar by a cord such as a length of elastic tubing or a length of suture. The proximal end of the envelope may also be secured to the collar in other equivalent manners.

The collar 210 is similar to previously described embodiments of the second collar. It may also be releasably connected to a first collar such as that shown in FIGS. 1–4 and 5–8. Alternatively, the lower end 216 of the collar may be inserted directly into the tissue incision 218 as shown in FIG. 26. The incision 218 made through the body tissue 220 would be smaller than the periphery of the collar lower end 216 so that the tissue surrounding the incision is stretched to fit around the collar. The collar 210 would then be secured in place on the body tissue 220 and extending into the incision 218 by a plurality of sutures 222 passing through the tissue and the collar around the periphery or the collar. Alternatively, the collar could be secured in place extending into the incision by adhesive tape or other equivalent means.

The envelope 208 of the FIG. 26 embodiment differs from previously described embodiments in that a second opening 224 and a third opening 226 are provided in the envelope and are sealed closed by opposed tongue and groove flexible strips 228, 230, of the type employed on Ziploc® brand plastic bags. The opposed tongue 228 and groove 230 flexible strips, shown opened at the second opening 224 and closed at the third opening 226, provide two closures in the envelope 208 that are easily opened and closed as needed. Furthermore, in their closed positions they provide a sufficient seal to maintain insufflation pressure in the body cavity and the envelope interior. Providing the two tongue and groove closures at the second 224 and third 226 openings enables the surgeon's hand to be inserted through one opening and the opening sealed closed around the surgeon's wrist either by closing the tongue and groove strips or securing the envelope adjacent the second opening closed around the surgeon's wrist with a flexible cord as employed in the previous embodiments. With the envelope secured closed around the surgeon's wrist, as different instruments are needed by the surgeon these instruments can be removed from the envelope interior and inserted into the interior where they can be grasped by the surgeon's hand through the third opening 226.

Each of the later described embodiments of the invention is used in the same manner as the first described embodiment in providing access for a hand or instrument through a body tissue incision while maintaining insufflation pressure or a pneumoperitoneum within the body. Additionally, the apparatus of the invention may be employed by containing each of the instruments intended to be used in a minimally invasive surgical operation within their own envelope of the apparatus. The second collar 4 of each envelope would then enable the instruments, contained in their own envelope, to be quickly connected with the first collar 2 as needed during the course of the operation. The first collar 2 would be provided with a valve structure in its interior, for example, a stricture or some other equivalent type of valve within the interior bore of the first elastomeric collar to close and seal the bore as instruments in their own envelopes are removed from and attached to the first collar. The quick connect releasable connection of the first and second collars described above may also be replaced by other known types of connections, for example, a bayonet-type connection that enable the first and second collars to be quickly connected and disconnected as desired. Furthermore, the size of the envelope can be substantially increased from that shown in the drawing figures so that several instruments needed to perform a particular operation may be contained in the one envelope. This would enable the surgeon to pick up and use the instruments contained in the envelope as needed without breaking the seal in the wall of the envelope or around the surgeon's wrist to remove instruments from the envelope or insert additional instruments into the envelope.

Although the invention has been described by reference to specific embodiments, it should be understood that other variations and adaptations of the invention can be made without departing from the intended scope of the invention defined by the following claims.

What is claimed is:

1. A surgical apparatus for providing access to a body cavity of a patient through an incision, the apparatus comprising:

a first member having a portion configured for attachment to the patient and a first coupling disposed proximate the portion, the first member defining a passageway for accessing the body cavity through the incision, wherein the passageway has a diameter sufficient to pass a surgeon's hand;

a second member including a second coupling configured for releasable attachment to the first coupling and a flexible portion configured to extend into the passageway and surround a surgeon's arm passing through the passageway, said flexible portion comprises a sealable opening configured to receive and seal around the surgeon's arm wherein the sealable opening is configured to be seal closed in the absence of the surgeon's arm; and wherein the portion of the first member configured for attachment to the patient is dimensioned to be inserted into the incision, and wherein the first member has axially opposite proximal and distal ends, wherein the first coupling is at the distal end and the portion for attachment to the patient is at the proximal end and comprises an annular rim that is insertable through the incision to underlie the tissue with the first member projecting through the incision to secure and seal the first member to body tissue surrounding the incision.

* * * * *